(12) United States Patent
Sottas et al.

(10) Patent No.: US 11,348,687 B2
(45) Date of Patent: May 31, 2022

(54) PERSONALIZING A BIOMARKER SIGNAL AND MEDICAL PROCEDURES BY DETERMINING PLASMA VOLUME VARIATION OF ONE OR MORE MARKERS

(71) Applicant: Biostarks Europe Sàrl, Geneva (CH)

(72) Inventors: Pierre-Edouard Sottas, Preverenges (CH); Yorck Olaf Schumacher, Buchenbach (DE); Louisa Lobigs, Rainbow Beach (AU)

(73) Assignee: Biostarks Europe Sàrl, Geneva (CH)

( * ) Notice: Subject to any disclaimer, the term of this patent is extended or adjusted under 35 U.S.C. 154(b) by 895 days.

(21) Appl. No.: 15/768,073

(22) PCT Filed: Oct. 21, 2016

(86) PCT No.: PCT/EP2016/075422
§ 371 (c)(1),
(2) Date: Apr. 13, 2018

(87) PCT Pub. No.: WO2017/068146
PCT Pub. Date: Apr. 27, 2017

(65) Prior Publication Data
US 2018/0308581 A1    Oct. 25, 2018

Related U.S. Application Data

(60) Provisional application No. 62/244,957, filed on Oct. 22, 2015.

(51) Int. Cl.
*G16H 50/20* (2018.01)
*G16Z 99/00* (2019.01)
*G16H 50/30* (2018.01)

(52) U.S. Cl.
CPC ............ *G16H 50/20* (2018.01); *G16Z 99/00* (2019.02); *G16H 50/30* (2018.01)

(58) Field of Classification Search
None
See application file for complete search history.

(56) References Cited

FOREIGN PATENT DOCUMENTS

WO      2017068146 A1    4/2017

OTHER PUBLICATIONS

Pierre-Edouard Sottas et al: "Adaptive Bayesian Approach to Clinical Trial Renal Impairment Biomarker Signal from Urea and Creatinine" International Journal of Biological Sciences, vol. 9, No. 2, Jan. 1, 2013 (Jan. 1, 2013), pp. 156-163, XP55331900, Australia ISSN: 1449-2288, DOI: 10.7150/ijbs.5225 Abstract, pp. 157-159, Discussion.
Benjamin J. Ryan et al: "AltitudeOmics: Rapid Hemoglobin Mass Alterations with Early Acclimatization to and De-Acclimatization from 5260 m in Healthy Humans", PLOS One, vol. 9, No. 10, Oct. 1, 2014 (Oct. 1, 2014), p. e108788, XP055333164, DOI: 10.1371/journal.pone. 0108788 p. 3.

*Primary Examiner* — G Steven Vanni
(74) *Attorney, Agent, or Firm* — Dinsmore & Shohl LLP; Weston R. Gould

(57) ABSTRACT

The present invention relates to a method of enhancing the detection of a signal from biomarker data in a subject or group of subjects.

13 Claims, 5 Drawing Sheets

A

B

PERSONALIZING A BIOMARKER SIGNAL AND MEDICAL PROCEDURES BY DETERMINING PLASMA VOLUME VARIATION OF ONE OR MORE MARKERS

FIELD OF THE INVENTION

The present invention generally relates to a method to personalize a biomarker signal and to medical procedures using the same. More particularly, the invention relates to a method of enhancing the detection of a signal from biomarker data in a subject or group of subjects.

BACKGROUND OF THE INVENTION

Biological markers are increasingly used in medicine to characterize a disease and act upon it. They often represent molecules measured in biological samples such as body fluids or tissues, such as a laboratory analyte that a physician can use to help make decisions in the diagnosis, prognosis and treatment of a disease.

The performance of a biomarker is mainly characterized by (1) its sensitivity, for a diagnostic biomarker this corresponds to its ability to detect a disease when the patient truly has the disease, and (2) by its specificity, for a diagnostic biomarker its ability to correctly determine that the subject does not have a disease and does not make false positives. When the prevalence of a disease is known or can be estimated, the Positive Predictive Value (PPV) and Negative Predictive Value (NPV) represent other relevant statistics to describe the performance of a biomarker using Bayes' theorem. When the biomarker is a quantitative value measured in a biological specimen by a clinical laboratory, reference ranges are often used to characterize a healthy condition with values outside the reference ranges as indicators of a disease. Reference ranges are usually represented by an interval that includes 95% of healthy subjects. In that case, the specificity of the biomarker is equal to 95% by design, meaning that by definition about 5% of healthy subjects have observations falling outside the reference interval.

Stratification is a method that allows the derivation of reference ranges on a sub-group of the general population. For example, stratification according to gender takes into account the heterogenous factor "gender" to derive different 95%-reference ranges for males and females. For example, hemoglobin in females is known to be 16 g/L less than in males and therefore reference ranges for females are usually 16 g/L lower than for males.

Stratification is a simple method that allows moving from a general population to a sub-population. The derivation of sub-groups reference ranges represent a first step in the individualization of a biomarker. From a statistical perspective, stratification allows the removal of between-subject biological variations.

The recent advances in both genetics and genomics have facilitated the access to genetic and genomic information for a single individual. This information can also be used to personalize a biomarker signal: when the biological pathway between a gene and a biomolecule such as a protein or a metabolite is known, and when the latter protein and metabolite is used as a biomarker, information about the gene and/or its transcript can be used to derive reference ranges that are specific to the group of subject who present this gene and/or transcript. From a statistical perspective, to use information about the genotype in order to stratify a phenotypic biomarker signal represents another method to remove between-subject variations. This method is particularly interesting for phenotypic biomolecules that are known to depend on the existence of protein-coding genes, for example for all families of metabolites associated to phase I and II metabolisms and excretion. In practice, gene- or transcript-specific reference ranges can be defined according to the genotype or genome of a single individual. In the same way as personalized medicine allows the choice of the right treatment according to genotypic and/or phenotypic differences, the same information can be used to personalize a biomarker signal and improve its general performance.

The ultimate method to remove between-subject variations and in turn derive true personal reference ranges is a longitudinal approach in which a series of baseline values are measured on a single individual. In case of a biomarker of disease, baseline values obtained when the subject is in a healthy condition can be used as personal references. In other words, the subject is used as his own reference and any heterogenous factor, such as age and gender, as well as any genetic characteristic, are intrinsically expressed through the baseline values. For example, the method called Reference Change Value (RCV) uses some prior knowledge about within- and between-subject biological variations and analytical uncertainty, all given as a coefficient of variation (CV), to assess the significance of differences in serial results from an individual. Although RCV is a method that is increasingly used in the clinics, it makes several assumptions, such as the underlying sources of variations must be well represented by a CV given in percent of a mean value, that are not tenable for many common biomarkers.

The method presented here allows the true personalization of a biomarker signal in combining, and therefore generalizing, all methods of stratification, personalization based on genetic and genomic information, and personalization based on a series of values measured in a single individual as described above. The method can be applied to any biomarker value, would it be (1) qualitative, for example presence or absence of a biomolecule in a biological fluid or tissue, (2) discrete, for example a biomarker that can take several discrete values that summarize the information available in a medical image obtained by diagnostic radiography, or (3) continuous as the result of a laboratory value measured in a biological fluid or tissue.

Interestingly, the method of the invention does not require full knowledge of heterogeneous factors, biological pathways, personal genetic or genomic information and/or previous individual biomarker values, the method makes the best decision with partial knowledge and information about the subject. Finally, for phenotypic biomarkers known to be associated to biologic or metabolic pathways, information about the genotype or the genome are not required for an individual in particular as soon as several observations of the phenotypic biomarker are obtained on this individual. The latter is made possible because the individual genotype or individual genome can be inferred from the phenotypic biomarker values following the effect to cause—and not usual cause to effect—relationship using Bayesian inference. This property of genetic inference from the phenotype is particularly interesting because most common biomarkers measured in routine in clinical laboratories are phenotypic biomarkers.

SUMMARY OF THE INVENTION

Figure 1:
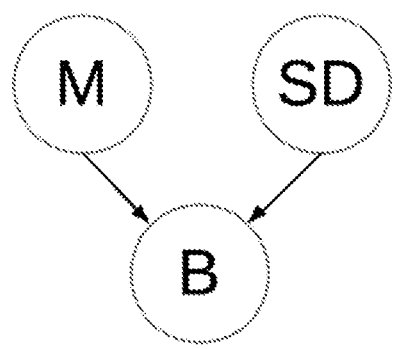
FIG. 1 is a geographical representation of a Bayesian network. M: mean, SD: standard deviation, B: biomarker, GT: genotype; G: gender and A: age.
Figure 1:
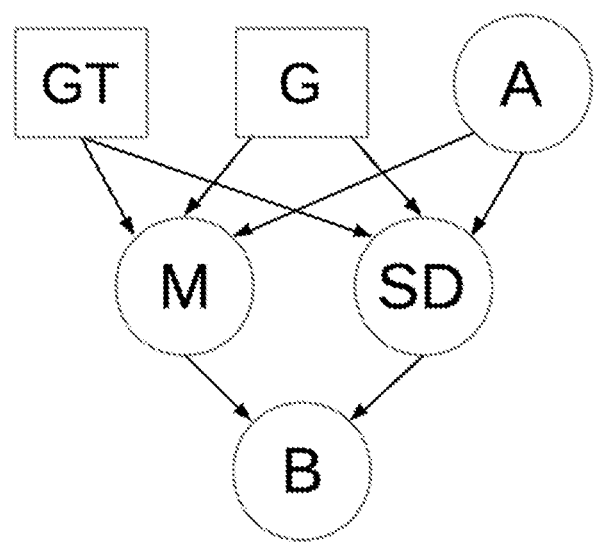

The present invention relates to a method of enhancing the detection of a signal from biomarker data in a subject or group of subjects comprising the steps of
  i) measuring zero, one or more values of one or more markers M from said subject or group of subjects,
  ii) applying an adaptive Bayesian model on the zero, one or more values measured for the one or more markers of step i) to derive individual distributions of expected values for each marker M in said subject or group of subjects,
  iii) deriving from said individual distributions some individual reference Z scores and individual reference ranges for a given specificity level for each marker M,
  iv) measuring one or more additional values for one or more markers M in said subject or group of subjects,
  v) comparing said one or more measured values to said one or more individual reference Z score and individual reference ranges,
wherein a deviation of said one or more measured values from said one or more individual reference Z scores and ranges is indicative of biological or physiological condition or variation in said subject or group of subjects.

Also provided is a method of determining plasma volume variation in a subject comprising the steps of
  i) measuring values of one or more markers M in a full blood sample and/or in a serum sample obtained from said subject, wherein said one or more markers are selected from the group comprising Hemoglobin Concentration (HbC), Transferrin, Creatinine, Platelets, Low-Density Lipoprotein (LDL), Albumin, Total Protein, Calcium, Cholesterol, Triglycerides, Thyroxine, White Blood Cells, plateletcrit (PCT), Neutrophils and Monocytes,
  ii) applying an adaptive Bayesian model on the values measured for the one or more markers of step i) to derive individual Z scores for each marker M,
  iii) deriving from said individual Z scores for each marker M a Z-score associated to plasma volume,
  iv) comparing said Z score associated to plasma volume to one or more pre-selected reference Z scores,
wherein a deviation of said Z score to one or more pre-selected reference Z scores is indicative of plasma volume variation.

DESCRIPTION OF THE INVENTION

A method of the invention concerns a method of enhancing the detection of a signal from biomarker data in a subject or group of subjects comprising the steps of
  i) measuring zero, one or more values of one or more markers M from said subject or group of subjects,
  ii) applying an adaptive Bayesian model on the zero, one or more values measured for the one or more markers of step i) to derive individual distributions of expected values for each marker M in said subject or group of subjects,
  iii) deriving from said individual distributions some individual reference Z scores and individual reference ranges for a given specificity level for each marker M,
  iv) measuring one or more additional values for one or more markers M in said subject or group of subjects,
  v) comparing said one or more measured values to said one or more individual reference Z score and individual reference ranges,
wherein a deviation of said one or more measured values from said one or more individual reference Z scores and ranges is indicative of biological or physiological condition or variation in said subject or group of subjects.

The method relies on Bayesian statistics and adapts when new information is available for a given subject using Bayesian inference techniques. The method is generic and can be applied to model any type of biomarker data and in turn make decisions for a unique individual, a group of subjects or a general population.

The method can be viewed as a Bayesian network that contains two mandatory layers of nodes that model the variations associated to a given biomarker. Optional layers can be added. The variations can be of any origin, such as biological and analytical. A probability distribution function modeling these variations as well as the hyper-parameters associated to these variations is associated to each node. In its simplest form, the Bayesian network consists in 3 nodes: a node B that represents the values of a biomarker in a single subject, and two nodes that represent, respectively, the individual mean M and individual standard deviation (SD) of these values. Such a network assumes that the biomarker values are normally distributed in the population of interest. A graphical representation is shown in FIG. 1A. Universal within-subject variations can be further assumed when the probability distribution function associated to node SD degenerates into a unique value. Conversely, a non-degenerated distribution associated to SD assumes that all subjects may present within-subject variations. The probability distribution associated to M can also assumed to be normal and in that case its standard deviation models between-subject variations.

Any types of distribution can be assumed given the knowledge that exists in the variations of a given biomarker in a given population. If the distribution is parametric, then the second layer models the parameters of this distribution. For example, if the within- and between-subject variations are given as a CV, such as given in the following database of biological variations for a large panel of biomarkers, see www.westgard.com/biodatabase1, then an additional node "CV" can be added to the network with links to the nodes M and SD, since CV is by definition equal to SD/M. Alternatively, log-normality of either or both within- and between-subject variations can be assumed.

The method is general enough to allow the modeling of the disentanglement of analytical and biological variations associated to a given biomarker. For example, when the biological within-subject variations is known to be well represented by a normal distribution while the analytical uncertainty is given as a CV representing a total error or estimated from test-retest experiments, a first layer models the biological variations, a second layer the analytical uncertainty, since the analytical uncertainty associated to the measurement of a biomarker value is on top of biological variations. In other words, the methods can model the analytical uncertainty associated not only to a mean value, a limiting assumption often made in error modeling, but also the effect of the analytical uncertainty when the true value of a biomarker differs from the mean because of natural biological variations.

Other optional nodes can be added in a top layer to model the effect of heterogenous factors on the biomarker values as shown in FIG. 1B. Examples include gender, age, ethnicity and body mass. The model can also integrate knowledge that exists on biological pathways associated to a biomarker, for example when genetic polymorphisms are known to affect the metabolism of a given biological compound. In other words, the Bayesian network can model the links that exist between a given genotype and its corresponding phenotype. For example, the metabolism of phase II of many biological compounds that are used as biomarkers of disease is known to be highly dependent on the activity of some enzymes, such as sulphatases and glucuronidases. Any genetic polymorphisms associated to these enzymes can be included in the network as soon as their effect on the values of the biomarker can be modeled, both qualitatively and quantitatively. For example, the concentrations of steroid hormones measured in urine depend on the insertion or deletion of genes such as UGT2B17 and UGT2B7. In particular, the concentration of testosterone glucuronide, the main metabolite of testosterone, is about 10 times lower in subjects who present a double deletion in UGT2B17 than in subjects who present a single or no deletion at all. In that example, the probability distribution function associated to M can be made dependent on a dichotomous node UGT2B17, with UGT2B17 being either "deletion" or "insertion", with the mean value of the distribution being 10 times when UGT2B17 is "insertion" than "deletion".

In one aspect, the model can be used to predict the expected values of a given biomarker for a single individual based on prior knowledge of the effect of the heterogenous factors on the biomarker as well as prior knowledge on the different types of variations associated to the biomarker. Any information on the individual can be then added as evidence in the network and all probability distribution functions updated using standard Bayesian inference techniques. For example, if it is known that the individual is a male, stratification can be performed with distribution functions changing from a general population to a male population. Similarly, any measured value of the biomarker can be added as evidence in the Bayesian network.

Another aspect of the invention consists in the longitudinal follow-up of biomarker values in a single individual with the derivation of reference ranges that make the best of available information on that individual. Reference ranges can be obtained assuming a given specificity of the biomarker when the probability distributions are given for a population of healthy subjects. For example, traditional reference ranges assume that 95% of normal healthy subjects have values falling in this interval. Higher specificity levels, such as 99% or 99.9%, can be chosen, for example when the biomarker is a diagnostics and over-diagnosis known to be an issue. This flexibility makes the method particularly suited to deal with over-diagnosis. The probability distributions are predictive in the sense that they are given before the measurement of a biomarker value. When a new observation is obtained, for example as part of a laboratory test, it can be checked whether the measured value falls within the specified interval. Any value falling outside the interval is not in agreement with the result of a normal physiological condition when the probability distributions are given for a population of healthy subjects. For a biomarker of disease, this information can be used by a physician to make improved decisions in the diagnosis, prognosis and treatment of a disease.

Figure 2:
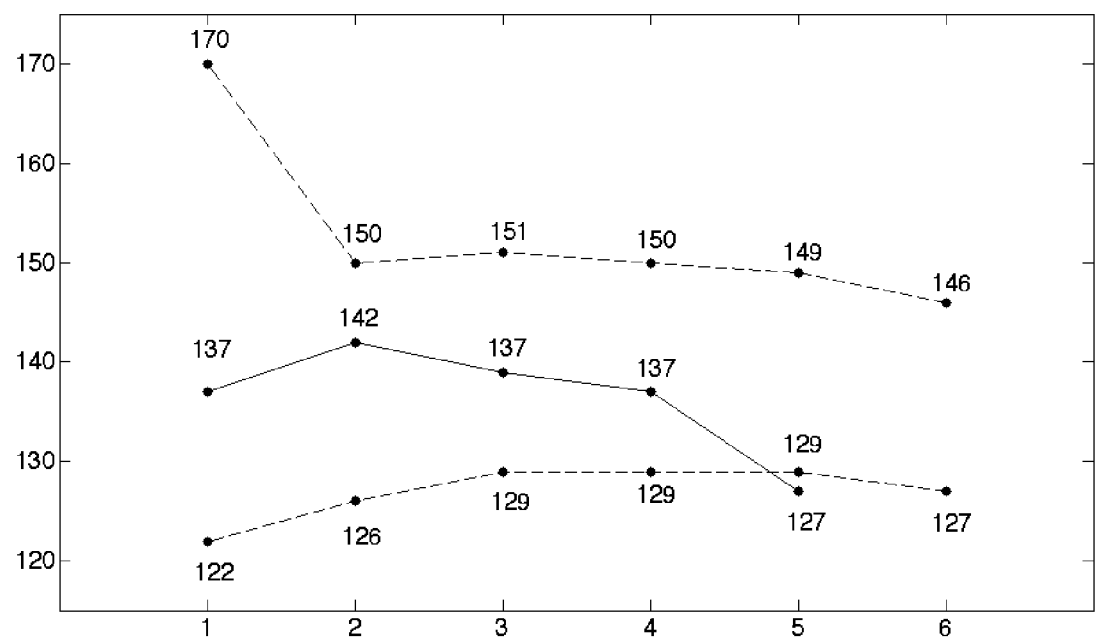
FIG. 2 shows personalized reference ranges of hemoglobin concentration for a male patient aged 55 years. Solid lines: 99%-reference ranges. Dashed line: actual results.

Then, the measured value can be entered as hard evidence in the Bayesian network. With this new evidence, prior distributions move to posterior distributions using Bayesian inference and in turn generate new reference intervals that can be used for a next test. During that process, some between-subject variations are removed and the posterior distributions become more specific to the individual and less to the population. For a first test, the initial reference ranges are population reference ranges. The inclusion of heterogenous factors in the Bayesian network naturally leads to stratified reference ranges. As soon as values measured on a same individual are added one after each other as hard evidence, the population reference ranges adaptively move to individual reference ranges. FIG. 2 shows an example for the hemoglobin concentration (Hgb) for a male subject aged 55 years who was tested at 5 occasions, namely Hgb=[137 142 139 137 127]. The last value, while remaining in reference ranges defined for males of this age, is lower than the lower value of the subject's reference interval and therefore is atypically low for this subject for a specificity as high as 99%. This example shows that the method allows an improvement in both sensitivity and specificity as compared to the use of traditional reference ranges. In particular, the derivation of personal reference ranges of a biomarker can make a dramatic improvement to detect a biological signal with a biomarker that presents significantly lower within- than between-subject biological variations.

For example, and despite that serum creatinine is the most commonly used biomarker of renal dysfunction, up to 60% of total kidney function can be lost before serum creatinine becomes out of population-based reference ranges. Serum creatinine presents significantly higher between- than within-subject variations (within-subject $CVi=5.95$, between-subject $CVg=14.7$), which is explained by a large heterogeneity according to gender, age and muscle mass. The application of the method allows the personalization of serum creatinine data with the derivation of personal reference ranges that significantly improve the detection of a signal associated to renal dysfunction. For example, in a population of 50 patients with chronic kidney disease of stage 2 or 3, a loss of [10-50]% in renal function, as obtained from direct measurements of glomerular filtration rate and clearance rate, is only detected in 7 patients using traditional reference ranges of serum creatinine (reference ranges stratified according to gender, namely [45-90] umol/L for women; [60-110] umol/L for men), whereas this loss is detected in 38 patients using the Bayesian network with the knowledge of gender, age, one healthy baseline and a specificity of 99%. The improved sensitivity of the method is particularly interesting for the early detection of kidney dysfunction. An early detection is important because the sooner kidney dysfunction is diagnosed and treated the greater chance of preserving remaining healthy nephrons, and preventing the need for subsequent dialysis.

In another aspect, the method is applied to biomarkers of, for example, liver to diagnose and monitor liver disease and more particularly liver fibrosis. Non-alcoholic fatty liver disease (NAFLD) is one of the causes of fatty liver and may progress to non-alcoholic steatohepatitis (NASH). Current main biomarkers of liver function, namely ALT, AST, ALT/AST, Fib-4, bilirubin, GGT, present all significantly higher between-subject biological variations than within-subject variations, which complicates their use as indicators of liver disease. In practice, small but important changes in a standard liver panel are difficult to detect because they are frequently observed within the population-based reference intervals. A male subject aged 42, without any symptoms associated to liver but considered as high risk to develop NASH because presenting hyperlipidemia and high blood pressure, was tested at 9 occasions for AST in a period of 8 years, with values of 17, 13, 17, 16, 20, 22, 18, 24, 28 U/L. Population-based reference ranges for AST are [8-40] U/L for males, meaning this patient never presented any value outside the reference ranges. The application of the method leads to initial stratified reference ranges of [10-38] U/L which are close to the population-based reference ranges. After 4 tests, the personalized reference interval as obtained by the Bayesian network is [9-25] U/L for a specificity of 99%. The second to last observation was 24 U/L, very close to the upper limit of the individual reference range, whereas the last value was 28 U/L, significantly higher than the upper value of the personal reference range. Although this last value was significantly below usual reference ranges, the application of the method show that this result cannot be the result of a normal physiological condition for a specificity of 99%. This information can be used by the physician to carry out additional analyses, such as a liver biopsy.

The large majority of biomarkers of disease present lower within- than between-subject biological variations. For example, up to 90% of the biomarkers measured in blood, serum and plasma listed in database www.westgard.com/biodatabase1 present lower within- than between-subject biological variations. This makes the use of personal reference ranges, as derived by the method described therein, a significant improvement over the use of traditional reference ranges for the detection of a biological signal for most biomarkers of disease. It should be noted that lower within- than between-subject variations is not a required property for a biomarker to apply the method. The method improves the signal for all biomarkers that present non-negligible between-subject variations, however the improvement that can be achieved by the method is associated to the ratio between between- and within-subject variations of the studied biomarker.

Another aspect of the invention provides the improved detection of a biological signal in clinical trials. Biomarkers have multiple functions in clinical trials: in addition to traditional indicators of disease, biomarkers are also used as indicators of response to drug treatment, such as markers of therapeutic safety and efficacy. Biomarkers can also turn into companion diagnostics to provide information for the effective use of a corresponding drug.

The very large majority of clinical trials use information collected within the course of the trial with sets of biomarkers collected for the enrollment as well as before, during and after drug treatment. For example, a subject is often enrolled in a trial based on specifications given on a set of biomarkers. The biomarker values obtained during the screening process are then often used in the trial as individual baseline values to which new sets of the same biomarker measured when the patient is treated can be confronted.

This framework makes the method particularly suited to improve the detection of a biological signal in clinical trials.

First, the method can be used to evaluate the biomarker data obtained during the trial to improve the early detection of a drug-induced signal and act upon it, such as a to decrease the dosage in dose-dependent trials. For example, the method can be used in early phase trials to detect a potential safety concerns on liver and renal functions, which represents two important causes of failure of early phase trials. To miss a drug-induced safety signal in phase I can lead to important costs in later phases in which the higher number of patients that are enrolled facilitate the detection of a drug effect. Undetected safety signals in early phases, but detected in late phases, is an important reason of clinical trial failure.

Second, the method can be used to decrease the number of patients to enroll in a trial to reach a given goal. Sample size calculations often neglect prior knowledge of components of variations of the biomarkers. The use of this information in the Bayesian network, together with the derivation of personal reference ranges for each subject enrolled in the trial, facilitate the detection of small drug-induced changes and in turn need less patients to reach the same statistical power as when traditional reference ranges are used. If prior information on the variations of the biomarkers is not readily available, because components of variations of many biomarkers are less available in patients with disease, these components of variations should be first estimated from the set of pre-screening, screening and baseline values obtained before drug treatment using standard methods for the analysis of variance. These group estimates are then introduced as parameters of the Bayesian network to derive true personal reference ranges. For example, glycated hemoglobin (HbA1c) represents today gold-standard in the diagnosis and management of diabetes mellitus because it is proportional to average blood glucose concentration over the previous weeks or months. The method can be used to improve the detection of a decrease in HbA1c in a phase III trial, alternatively to decrease the number of patients required to reach a given goal for the same statistical power. Table 1 (Example 1) presents the number of subjects required to detect a decrease of 0.1% in HbA1c with either a balance 1:1 or unbalanced 2:1 design for a power of 99% and a significance level of 0.05. Three methods to evaluate a biological signal are compared: (1) a traditional sample size calculation based on Student's T-test, (1) an analysis of covariance with a set of screening values as covariates, and (3) the method presented here. An important reduction in the number of control subjects is achieved with the Bayesian method, from 1075 to 150, corresponding to 1:1 and 7:1 designs, or from 790 to 139, corresponding to 2:1 to 11:1 designs.

Third, the method can be used in clinical trials to select the good responders to a drug treatment from a general population. To find the right drug to the right patient is central to personalized medicine, however today framework of drug development based on a succession of phases that evaluate the safety and efficacy of a drug presents strong limitations to find the good responders to a drug based on biological data. The derivation of personal reference ranges on biomarkers of therapeutic safety and efficacy, without loss of generality to phases 0, I, II, III or IV, allows the personalization of the evaluation of a drug-induced effect, and in turn the selection of the sub-populations of patients who respond and do not respond to the drug.

Fourth, the method can be used to facilitate the discovery and validation of companion diagnostic markers. The advent of personalized medicine and its associated demands for individualized therapeutic agents has increased the costs of drug development. Central to the development of companion diagnostics is the possibility to find biological characteristics, would it be genotypic or phenotypic, on a group of patients, or ideally at the individual level. The method can be first used to define groups of responders and non-responders based on personalized biomarker data obtained as part of a clinical trial. Genome-wide or phenome-wide associations studies can be then applied on these two groups of subjects to identify genotypic or phenotypic biomarkers that can serve as companion diagnostics.

Another aspect concerns the inference of genetic polymorphisms from the measurement of phenotypic biomarkers in a single individual. For example the presence or absence of a coding gene may have important consequences on the production of related proteins and other metabolites. The measured concentrations of the latter proteins and metabolites are entered as hard evidence in the method and inference techniques used to go against the causal direction to return posterior probability distributions of the presence or absence of the gene. For example, the introduction of the concentration of the glucuronide metabolite of testosterone in urine in a Bayesian network that links the gene UGT2B17 to the protein glucuronidase, then the protein to the glucuronide metabolite, allows the determination of the presence or absence of the gene UGT2B17. In other words, the method makes possible the knowledge of genetic characteristic of a given individual from the measurement of phenotypic biomarkers associated to this gene. Genetic information is inferred rather than measured. The knowledge of individual genetic characteristics allow then the derivation of personal reference ranges in which the between-subject variations associated to the genetic characteristics are removed.

An aspect of the method of the invention relates to a method of determining plasma volume variation in a subject comprising the steps of
  i) measuring values of one or more markers M in a full blood sample and/or in a serum sample obtained from said subject, wherein said one or more markers are selected from the group comprising Hemoglobin Concentration (HbC), Transferrin, Creatinine, Platelets, Low-Density Lipoprotein (LDL), Albumin, Total Protein, Calcium, Cholesterol, Triglycerides, Thyroxine, White Blood Cells, plateletcrit (PCT), Neutrophils and Monocytes,
  ii) applying an adaptive Bayesian model on the values measured for the one or more markers of step i) to derive individual Z scores for each marker M,
  iii) deriving from said individual Z scores for each marker M a Z-score associated to plasma volume,
  iv) comparing said Z score associated to plasma volume to one or more pre-selected reference Z scores,
wherein a deviation of said Z score to one or more pre-selected reference Z scores is indicative of plasma volume variation.

Plasma Volume, the liquid component of the blood, plays a crucial role in countless physiological processes and is an important variable for many clinical decisions. Dialysis in patients with chronic kidney disease (CKD) is based on the removal of a defined amount of intravascular fluid. Intensive care or heart failure patients require a strict fluid monitoring to improve their health outcome. However, there is yet no practically applicable method to accurately measure plasma volume. Most direct tests rely on indicator dilution methods, are cumbersome in methodology and thus impracticable for clinical practice. For these reasons, plasma volume is mostly indirectly estimated using concentration based blood measures such as the hematocrit and the concentration of hemoglobin, which are evaluated longitudinally, and changes in these variables are attributed to shifts in plasma volume. Such methods have obvious flaws and are only of limited utility in situations where the red cell mass is not guaranteed to be stable and might change, such as in intensive care patients with bleedings, dialysis patients who might have a renal anemia etc.

Red cell volume, the component of the blood composed of erythrocytes, is the principal means of delivering oxygen to the body tissues. Concentration-based blood measures obtained as part of a full blood count are used as indicators of an altered erythropoiesis. For example, WHO has specified some thresholds on the concentration of hemoglobin (HbC) to define anemia. This neglects the fact that HbC can be low because of a high plasma volume rather than a true decrease in red cell mass. This pseudo-anemia is observed in patients with kidney disease, as an adaptation to aerobic exercise in athletes, in deliberate hypotensive anesthesia in intensive care, etc. . . The measurement of red cell mass can be performed after the injection of radioactive markers or carbon monoxide (CO) in the body but these methods are impracticable in daily clinical practice. A method that provides a robust estimation of the red cell mass or volume from a simple blood test, or at least a substantive target that can be used to titrate the dose of an erythropoiesis stimulating agent, is still lacking today.

The lack of practical methods to estimate both plasma and red cell volumes is particularly problematic to monitor patient suffering from renal failure such as, e.g. Chronic Kidney Disease (CKD) patients. This is related to the two main functions of the kidney: to balance the body fluid's and to control the erythropoiesis through the production of erythropoietin. Dialysis—to remove excess water—and treatment with recombinant erythropoietin (rEPO)—to fight against anemia—are the two main pillars of CKD management. Unfortunately, it is not possible to know from an increase in concentration-based blood measures whether the cause was an increase in red cell volume—e.g. a patient responds well to rEPO treatment—or a decrease in plasma volume—e.g. not enough fluid removed. The same applies for a decrease in these variables.

Also, an increase in red cell volume and/or plasma volume will increase blood pressure and in turn the risk of complications such as heart attacks and strokes. In practice, the bad monitoring of plasma volume with not enough fluid removed via dialysis, with is often incorrectly compensated by higher doses of rEPO to meet a given hemoglobin concentration target, leads to a significant increase in blood volume, the main reason for high blood pressure and subsequently death in patients with CKD.

A reliable method to estimate changes in both red cell and plasma volumes is required to improve the clinical decision making in many different settings. Fluid management in intensive care patients could be improved and the true red cell and plasma volumes component of the blood picture of a patient undergoing dialysis and rEPO treatment could be estimated, thereby improving his management. The method presented therein allows the derivation of markers of red cell, plasma and blood volumes from a simple blood test based on the consistency of the changes over time in a set of concentration-based variables after the removal of undesired between-subject variations with the adaptive Bayesian model. The direct measurement of red cell mass and plasma volume, although cumbersome and impracticable for routine clinical practice, were used here as a reference method to validate the approach. The end products are markers of both red cell volume and plasma volume that can be readily be obtained in a clinical setting from a simple blood test to monitor a patient's fluid balance and erythropoiesis.

The method as described above generally comprises the following Steps:

Steps 1.1 to 1.3 consist in initial measurements and/or calculations to assist in the use of the method for which one application is described in Steps 2.1 to 2.6. Although Steps 1.1 to 1.3 represent the preferred way to collect prior information for the application of the method, the method remains applicable when only partial information is gathered during Steps 1.1 to 1.3. In particular, reference targets of red cell, plasma and blood volumes can be set by a person with expertise in the area using conventional estimation methods based on population references.

(1.1) To define physiological targets for red cell, plasma and blood volumes.

(1.1.1) When the subject is known to present a well controlled balance of red cell, plasma and blood volumes, physiological targets for red cell, plasma and blood volumes can be defined using a reference ad-hoc method capable to assess red cell volume, plasma and/or blood volumes, such as (but not limited to) indicator dilution methods, for example the joint measurement of Hemoglobin mass (HbM) by the CO-rebreathing method with the Hemoglobin Concentration (HbC) and mean corpuscular hemoglobin concentration (MCHC) in blood, using the following formula:

Red cell volume (L)÷HbM(g)÷(MCHC(g/dL)*10)

Blood volume (L)=HbM(g)÷(HbC(g/dL)*10÷0.91)

Plasma volume (L)=Blood volume (L)−Red cell volume (L)

(1.1.2) If targets of red cell, plasma and blood volumes cannot be achieved using a reference analytical method, decent targets should either be calculated from anthropometric characteristics, such as body mass, fat free body mass, height, age and gender or estimated based on published population references. For example, normal estimation averages of blood volume per kilo of body mass is 60-80 ml/kg. Similarly, targets for hemoglobin mass can be defined based on normal estimation averages of hemoglobin mass per kilo of fat free mass. The latter target for HbM can be further derived in a target for red cell volume given a population average of 33 g/dl for MCHC, or if available, a subject specific value of MCHC using the above formula. Alternatively, proper targets can be defined by a person with expertise in the area based on any information available on the subject, including anthropometric characteristics, previous tests results and medical history.

(1.2) When the patient is known to present a well-controlled balance of red cell, plasma and blood volumes, one or more markers selected from the non limiting group comprising HbC, Transferrin, Creatinine, Platelets, Low-Density Lipoprotein (LDL), Albumin and Total Protein, and, optionally, Calcium, Cholesterol, Triglycerides, Thyroxine, White Blood Cells, Plateletcrit, Neutrophils and Monocytes, are measured in two blood samples, preferably a full blood EDTA sample and a serum samples, collected from the subject. These two blood samples should preferably be collected at different times, preferably at least 5 days apart.

Alternatively, the analytical panel of one or more markers is selected from the non-limiting group comprising: HbC, Transferrin, Creatinine, Platelets, LDL, Albumin, Total Protein and Calcium.

(1.3) Individual expected distributions of all these markers, and, if available, HgC, red cell, plasma and blood volumes, are calculated using the Adaptive Bayesian model described herein. The Adaptive Bayesian model consists in a hierarchical Bayesian network that allows the derivation of individual distributions of any marker measured in a biological fluid, and in turn individual reference ranges at a given specificity level (e.g. 99%).

(2.1) Blood sample(s), including a full blood sample, a plasma sample and/or a serum sample, preferably a full blood EDTA sample and a serum sample, are collected on the subject. The set consisting of biological variables, preferably the set of the 8 markers given in Step 1.2, are measured together with MCHC. These markers of plasma volume are preferably measured in serum with a full blood count performed on full blood. Any additional test can be performed on the collected sample(s) for the monitoring of any concentration-based marker in blood (see Steps 2.5.3 and 2.5.4 below).

(2.2) The Adaptive Bayesian model is applied on the set of markers of plasma volume to derive Z-score for each marker. These Z-scores represent individual variations over individual means. This process is crucial to remove inter-individual variations and highlights the variations associated with changes in plasma volume.

Preferably, the individual Z scores for each marker Mi are determined by $$Z(Mi) = \frac{M(i) - ME(i, j)}{\sqrt{VAR(i, j)}}$$

where ME(i,j) is the individual mean for subject j, VAR (i,j) the individual variance for subject j and Mi represents the value of one of the marker at time i.

(2.3) The individual Z-scores are then combined using a weighting function derived from the known variations of each marker with plasma volume as well as from the consistency between all Z-scores. The outcome, given as a Z-score, is an estimate of the variations in plasma volume. This step comprises establishing a first estimate of the Z score (Z(Mi) estimate) associated to plasma volume calculated as the sum of the Z-scores of all biomarkers times the respective marker's coefficients, determining the residuals (R) in the variations associated to each observation Mi as, establishing a weighting function associated to the consistency between the variations in each marker M calculated as the normality probability distribution of the residuals in the variation of the markers, and calculating the Z score associated to plasma volume by weighting the estimate of the Z score (Z(Mi) estimate) with the weighting function.

A weighting function associated to the consistency between the variations in each marker is calculated as the normality probability distribution of the residuals in the variations of the markers. The second and final estimate Z-score associated to plasma volume shifts is calculated similarly as above, namely as the sum of the Z-scores computed for each biomarker times the markers' coefficients, except that the calculation is further weighted by the weighting function computed from the residuals.

In case the one or more markers are selected from the group comprising HbC, Transferrin, Creatinine, Platelets, Low-Density Lipoprotein (LDL), Albumin and Total Protein, and, optionally, Calcium, Cholesterol, Triglycerides, Thyroxine, White Blood Cells, Plateletcrit, Neutrophils and Monocytes, then the respective marker's coefficients are preferably about 0.30 for Hemoglobin C (HbC), about 0.23 for Transferrin, about 0.23 for Creatinine, about 0.25 for Platelets, about 0.13 for Low-Density Lipoprotein (LDL), about 0.25 for Albumin, about 0.31 for Total Protein, about 0.20 for Calcium, about 0.12 for Cholesterol, about 0.064 for Triglycerides, about 0.082 for Thyroxine, about 0.48 for White Blood Cells, about 0.28 for plateletcrit (PCT), about 0.19 for Neutrophils and about 0.39 for the Monocytes.

In case the one or more markers are selected from the group comprising Hemoglobin Concentration (HbC), Transferrin, Creatinine, Platelets, Low-Density Lipoprotein (LDL), Albumin, Total Protein and Calcium, the respective marker's coefficients are preferably about 0.43 for Hemoglobin C (HbC), about 0.32 for Transferrin, about 0.33 for Creatinine, about 0.33 for Platelets, about 0.20 for Low-Density Lipoprotein (LDL), about 0.38 for Albumin, about 0.47 for Total Protein, and about 0.31 for Calcium.

As used herein, the term "about" indicates a defined range around that value of +/−10%.

Since the markers are correlated with each other, their respective coefficients are different in case they are selected from the group comprising 8 or 15 markers.

Usually, a Z-score higher than zero means hemodilution, with values higher than about 2.3 indicating a strong hemodilution; a value lower than about zero a hemoconcentration, with values lower than about −2.3 indicating a strong hemoconcentration (for a specificity of 99%, other specificity levels can be chosen).

Preferably, a confidence level is associated to the Z-score. The confidence level is equal to the exponential of the sum of the weighting function. This confidence level is normalized between 0 and 1 so that values close to 0 have a low confidence while values close to 1 have a high confidence. The variance that is used to calculate the Z-score associated to plasma volume shifts is finally weighted by this confidence level.

Alternatively, the Z-score associated to plasma volume shifts can be further used to correct the initial markers by using scaling factors. For the version that uses 8 markers of plasma volume shifts, the correction is equal to the Z-score times 1.34, 1.57, 1.27, 1.33, 1.91, 1.30, 0.85, 1.78, respectively for Transferrin, Albumin, Calcium, Creatinine, Total Protein, Platelets, Low Density Lipoprotein and Hemoglobin. For the version that uses 15 markers, the correction has the following scaling factors: 0.72, 0.79, 0.62, 0.71, 0.98, 0.80, 0.39, 0.96, 0.33, 0.20, 0.25, 1.57, 0.89, 0.62, respectively for Transferrin, Albumin, Calcium, Creatinine, Total Protein, Platelets, Low Density Lipoprotein, Hemoglobin, Cholesterol, Triglycerides, Thyroxine, White Blood Cells, Plateletcrit, Neutrophils and Monocytes. Since the markers are correlated with each other, their respective scaling factors are different in case they are selected from the group comprising 8 or 15 markers.

(2.4) The plasma volume at the time of blood collection is estimated from the expected mean returned by the Adaptive model together with the estimated Z-score and confidence level. Estimates of the hemoglobin mass, red cell and blood volume can be further obtained using the formula given in Step 1.1 together with the actual HbC and MCHC test results.

(2.5.1) The estimated plasma volume can be used to specify an intervention on the plasma volume based on target(s) of plasma volume such as defined in Steps 1.1 to 1.3. In case of hemodilution, this includes any methods that aim to remove excess water from the blood, including hemodialysis, peritoneal dialysis, hemofiltration and their combinations.

In case of hemoconcentration, this includes any methods that aim to replenish the body's fluid balance such as any volume replacement therapies.

(2.5.2) The estimated red cell mass, and corresponding hemoglobin mass (HgB), can be used to specify an intervention on red cell mass based on target(s) of red cell mass and HgB such as defined in Steps 1.1 to 1.3. In case of true polycythemia caused by a too high red cell mass and/or HgM, this includes any methods that aims to remove excess red cells from the blood. In case of true anemia caused by a too low red cell mass and/or HgB, this includes any methods that aim to increase red cell mass to a normal level, either directly with blood transfusion methods and similar, or indirectly through the use of any erythropoietic stimulating agents.

(2.5.3) The estimated blood volume can be used to specify an intervention that aims to normalize blood volume based on blood volume target(s) such as defined in Steps 1.1 to 1.3. If the blood volume is too high, this includes blood withdrawal; in case the blood volume is too low, blood transfusion or the application of erythropoiesis stimulating agents.

(2.5.4) The estimated plasma volume can be used to normalize any analytical test performed in blood plasma or serum that is returned as a concentration. Hemoconcentration leads to falsely high values of the tests, hemodilution to falsely low values. In both cases, the affected value may wrongly suggest another cause, such as a medical condition. This normalization for plasma volume shifts in blood is similar to the correction by specific gravity in urine. This normalization is preferably performed after the application of the Adaptive Bayesian model to determine individual distributions and reference ranges of the measured value. Alternatively, if the Z-score indicates a hemoconcentration that corresponds to, for example, an increase of 28% over the expected plasma volume levels given in Step 2.4, the analytical result of the concentration-based marker can be corrected by dividing the measured value by 1.28.

(2.6) Steps 2.1 to 2.5 can be repeated for the continuous monitoring of red cell, plasma and blood volumes over time, as well as for the continuous monitoring of any concentration-based marker measured in plasma or serum that aims to include a correction for variations in plasma volume. This process is preferably performed using a statistical method that takes into account intra-individual variations of the marker, such as the Adaptive Bayesian model. The correction for plasma volume is integrated in the statistical model to remove the part of the variations that is caused by plasma volume shifts to return individual reference ranges corrected for plasma volume shifts.

The invention thus also contemplates an apparatus such as a device for implementing the methods of the invention. The method of the invention can run on any device that has a micro-processor, such as a computer, smartphone, tablet or internet server, with results returned in a fraction of a second even for the most complex situations in which genetic polymorphisms are inferred from the biomarker values.

EXAMPLES

Example 1

Algorithm

In the special case when the between- and within-subject variations of the biomarker are known to be well represented by a normal distribution, the method can be applied using a simple algorithm. The procedure and algorithm are given in Table 2. Otherwise, Bayesian inference techniques are required to run the method.

The method described in Table 2 is applied to evaluate the effect of a new drug treatment in an anemic patient participating to a phase III clinical trial. The patient is a woman aged 48 years enrolled in the trial based on a pre-screening value of 95 g/dL. A second screening value of 93 g/L is obtained before treatment. During the trial, the patient is tested at six occasions with values of 96, 101, 98, 107, 109 g/dL.

The population mean POP_ME is 106 g/L in males, 90 g/L in females for a group of anemic patients. The between-subject variance is 65 g2/L2, the within-subject 17 g2/L2. The predictive distribution of expected values for the first observation is normal with mean PRE_ME=90 and variance PRED_VAR=65+17=82. Assuming a 99% specificity, the minimal value of the reference interval (0.5 percentile) is equal to 90−2.58*sqrt(82)=67, the maximal value of the reference interval (99.5 percentile) equal to 90+2.58*sqrt(82)=113. The first observation RES(1)=95 falls inside the interval [67-113] g/L.

With RES(1)=95 g/L, the predictive distribution of expected values for the second observation can be calculated:

$A=65$ $B=90$ $X1=1/(1/65+1/17)=13.5$ $X2=13.5*90/65+13.5*95/17=94.1$ $PRED\_ME=94.1$ $PRED\_VAR=13.5+17=30.5$

The minimal value is equal to 94.1-2.58*sqrt(30.5)=80, the maximal value 94.1+2.58*sqrt(30.5)=108. The second observation RES(2)=94 g/L falls in the interval [80-108] g/L.

With RES(2)=93 g/L, a new iteration gives:

$A=13.5$ $B=94.1$ $X1=1/(1/13.5+1/17)=7.5$ $X2=7.5*94.1/13.5+7.5*93/17=93.3$ $PRED\_ME=93.3$ $PRED\_VAR=7.5+17=24.5$

The minimal value becomes 93.3-2.58*sqrt(24.5)=81, the maximal value 93.3-2.58*sqrt(24.5)=106. The personalized reference interval is [81-106] g/L for this patient and has been obtained before the administration of the drug. Any value outside this interval is not in agreement with the assumption of normal variations of Hgb for a specificity of 99%. Here the last two values at 107 and 109 g/L are significantly higher than the upper limit of the personalized reference interval. This suggests that the drug was effective for this patient. The method can be further applied iteratively for the values obtained during treatment in order to define personal reference ranges post-treatment. Alternatively, the personal reference ranges obtained during treatment can be used to make informed decisions during the trial in case of an adaptive design, such as to change the dosage of the drug in dose-escalating trials.

TABLE 1

Number of patients required to detect a decrease in 0.1% in HbA1c in phase III trial.

| Treatment Placebo | | | | | | |
|---|---|---|---|---|---|---|
| Student's T-test | | ANCOVA | | Method | | |
| # patients | # patients | Design | # patients | Design | # patients | Design |
| 1075 | 1075 | 1:1 | 218 | 5:1 | 150 | 7:1 |
| 1580 | 790 | 2:1 | 204 | 8:1 | 139 | 11:1 |

TABLE 2

Method to evaluate a biomarker that present variations that are normally distributed Definitions

| | |
|---|---|
| n | Number of biomarker values |
| RES(n) | Observation number n |
| POP_ME | Population mean after stratification |
| BS_VAR | Between-Subject variance |
| WS_VAR | Within-Subject variance |
| PRED_ME | Mean of the predictive distribution |
| PRED_VAR | Variance of the predictive distribution |
| LF | Likelihood function of a series of n values |

Algorithm

| | |
|---|---|
| n = 0 | X1 = BS_VAR<br>X2 = POP_ME<br>PRED_ME = X2<br>PRED_VAR = X1 + WS_VAR |
| n -> n + 1 | A = X1<br>B = X2<br>X1 = 1/(1/A + 1/WS_VAR)<br>X2 = X1*B/A + X1*RES(n)/WS_VAR<br>PRED_ME = X2<br>PRED_VAR = X1 + WS_VAR<br>The Likelihood function LF for the sequence of n observations can be further calculated as the negative logarithm of the multiplication of the standard normal distribution evaluated at the values of the sequence standardized by PRED_ME and PRED_VAR, divided my n minus 0.91894. The predictive distribution of LF is a Gamma function with shape parameter n/2 and scale parameter 1/n. |

Example 2

Method

Thirty three healthy subjects aged 25-53 were monitored over six months. The hemoglobin mass (HbM) of all subjects was determined using a CO-rebreathing method at the start of the study. On a monthly basis, a serum sample (10 mL BD serum vacutainer) and a whole blood sample (4 mL BD K2 EDTA vacutainer) were collected. Following blood collection, the participants performed the same CO-rebreathing method (Schmidt W, Prommer N. The optimised CO-rebreathing method: a new tool to determine total haemoglobin mass routinely. Eur J Appl Physiol. 2005 December; 95(5-6):486-95.) for the measurement of HbM. Times between monthly measures varied slightly with a minimum of 9 days and maximum of 56 days. The subjects' weight was also monitored. At month 6, after completion of the final venous blood collection and CO-rebreathing maneuver (performed as per the prior 5 months), the 33 subjects performed an exercise challenge designed to promote an acute, maximal increase in plasma volume. The exercise challenge involved a 30 min maximal step-test on a cycle ergometer under standard laboratory conditions. Immediately post, and 1 hour post exercise venous blood was collected.

All blood samples were analyzed or aliquoted within 1 hour of collection. A complete blood count analysis was performed in triplicate using a Sysmex XT 2000i analyser (Kobe, Japan). The following 27 indices were used in this study: Platelets (PLT), Hemoglobin Concentration (HbC), White Blood Cells (WBC), Red Blood Cells (RBC), Hematocrit (HCT), Mean Corpuscular Volume (MCV), Mean Corpuscular Hemoglobin (MCH), Mean Corpuscular Hemoglobin Concentration (MCHC), Red Cell Distribution Width Standard Deviation (RDW_SD), Red Cell Distribution Width Coefficient of Variation (RDW_CV), Platelet Distribution Width (PDW), Mean Platelet Volume (MPV), Platelets Large Cell Ratio (P_LCR), Plateletcrit (PCT), Neutrophils (NEUT), Monocytes (MONO), Eosinophils (EO), Basophils (BASO), Lymphocytes (LYMPH), Reticulocytes number (RET), Reticulocytes percentage (% RET), Low Fluorescence Reticulocytes (LFR), Medium Fluorescence Reticulocytes (MFR), High Fluorescence Reticulocytes (HFR), Immature Reticulocyte Fraction (IRF), Reticulocytes Hemoglobin content (RET_He), Red Blood Cells Hemoglobin content (RBC_He).

Serum samples were spun down at 4° C., 1500 rpm for 10 min, and aliquots stored at −80° C. All serum samples were analyzed in random order in batch analysis with a Dimension Integrated Chemistry System (Siemens, Germany). The following 18 chemistry variables, with known low biological variation, were analyzed: Transferrin, Alanine Aminotransferase, Albumin, Alkaline Phosphatase, Calcium, Chloride, Sodium, Creatinine, Free Thyroxine (FT4), Triodothyronine (T3), Thyroxine (T4), Total Protein, Magnesium, Potassium, Cholesterol, HDL, LDL and Triglyceride.

Red cell, plasma and blood volumes were calculated as follows:

Red cell volume=HbM(g)÷MCHC×100

Blood volume=HbM(g)×100÷HbC÷0.91

Plasma volume=Blood volume−Red cell volume

In total, 9 collections of 48 blood variables on 33 subjects led to 14'256 readings.

All data were analyzed with Matlab version 8.3. Analyses of variance with subject as group variable were performed on all 48 biomarkers to derive within- and between-subject components of variance. The adaptive Bayesian model was applied to remove between-subject components on all variables. The use of this model is key to find the biomarkers that present variations that are correlated to plasma volume shifts as well as to put the effect of plasma volume shifts on the same scale for each biomarker. A Z-score formalism is chosen, which each Z value corresponding to the number of standard deviations from the expected mean computed by the adaptive model. A principal component analysis was then used on the individualized biomarker data to check for consistency in plasma volume variations between all biomarkers. A multi-variate version of the adaptive model was finally developed to derive individualized values of biomarkers corrected for plasma volume variations. A leave-one-subject-out cross-validation procedure was used to limit overfitting and to guarantee a good generalization of the model on new subjects.

Results

Figure 3:
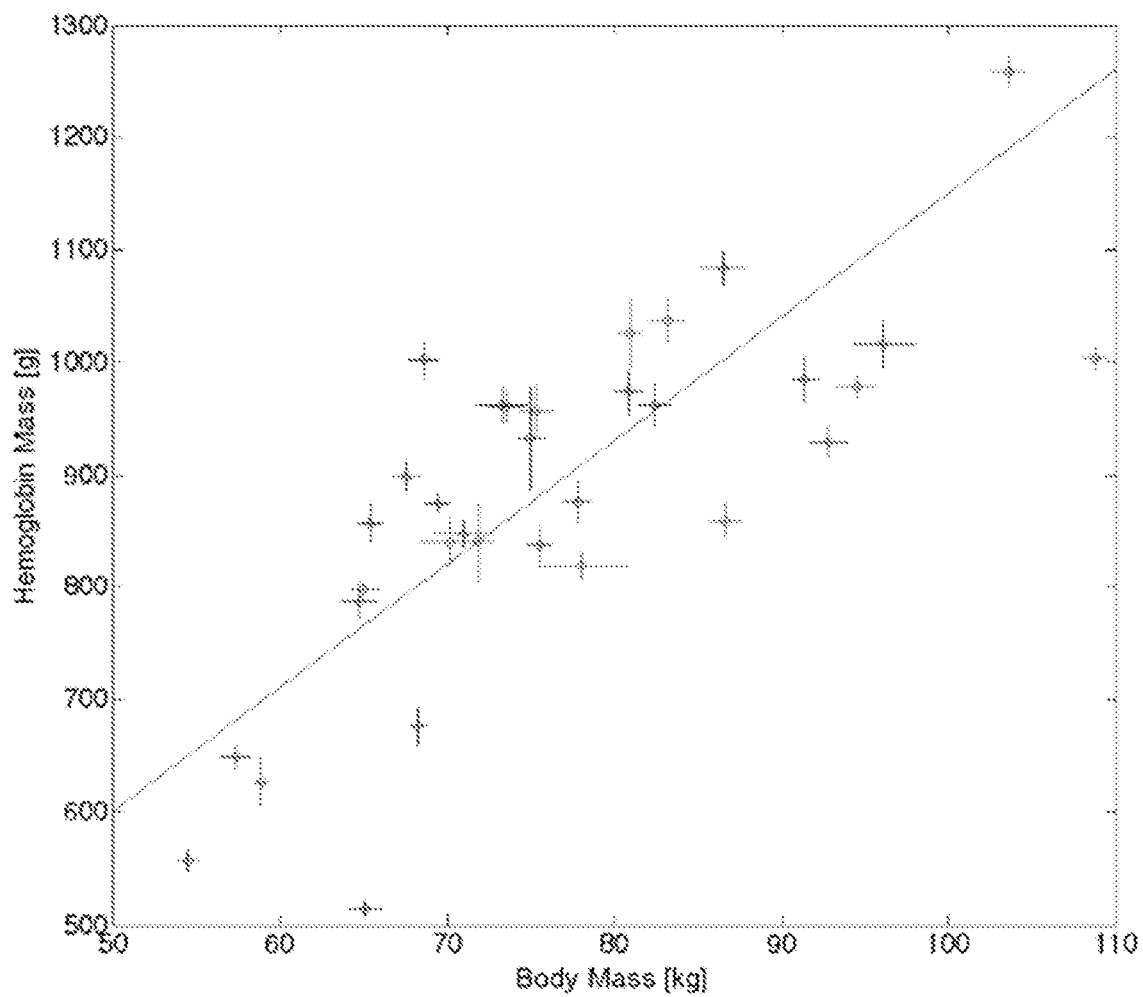
FIG. 3 shows the relation between hemoglobin mass measured by the CO-rebreathing method for 33 healthy subjects as a function of body mass. Points represent the average of 9 values measured over a 6-months period, the bars the standard deviations (X-axis: body mass, Y-axis: hemoglobin mass). Linear regression: Hbmass [g]=11*BodyMass [kg]+50, R2=0.61.

FIG. 3 shows the values of hemoglobin mass plotted against the body mass for all 33 subjects (R2=0.61). The mean, between- and within-subject components of variance are shown in Table 1 for all 48 variables. The data obtained after the acute exercise challenge were excluded from the analysis of variance because not representative of normal variations of the biomarkers. The adaptive Bayesian model was then applied on all variables with the calculated components of variance as parameters. A leave-one-subject-out cross-validation procedure was used to prevent the use of parameters derived from data coming from the same subject. The application of the adaptive model allows the removal of undesired between-subject variations and to greatly facilitate the detection of signals caused by plasma volume shifts.

The 18 serum-based biomarkers were chosen because presenting low within-subject variations as well as being available in most chemistry panels proposed by automated analyzers today, at the exception of Triglycerides and Free Thyroxine that are automatically proposed as part of a lipid, respectively thyroid, panel. At the exception of the two latter biomarkers as well as ALT, all 15 other biomarkers present lower within- than between-subject variations. All these 15 biomarkers present an intra-individual coefficient of variation that is lower than 10%, at the additional exception of ALP. The outputs of the adaptive model were given in the Z-score space to represent the variations over an individual expected mean. A universal within-subject variance was assumed here. This assumption is valid for healthy subjects and does not preclude the use of the model on patients with disease.

Unsurprisingly, salts (Na, Chloride, Calcium, Magnesium) presented the most stable profiles together with Total Protein and Albumin. However a good stability is not the only criterion that a biomarker should fulfill to exhibit a correlation with plasma volume. A linear regression analysis was performed between the Z-score values found after application of the adaptive model on plasma volume and the Z-score computed for all serum-based biomarkers. The regression analysis was performed with and without the values obtained following the acute exercise challenge (see Table 1 for the resulting p-values). When the exercise challenge data are taken into account, all 18 serum-based biomarkers showed a significant correlation with plasma volume at the notable exception of Chloride, FT4 and T3. When the exercise challenge data are excluded, HDL, ALT, ALP, Potassium, Magnesium, Sodium and Creatinine do not show anymore a significant correlation to plasma volume.

The same procedure was applied to all biomarkers obtained from the full blood count. Unsurprisingly, HbC showed low within-subject variations as well as a strong correlation to plasma volume.

A Principal Component Analysis was performed on various combinations of the 18 variables that present both low variations and a significant correlation to plasma volume. The goal is to explain the largest amount of the variance in plasma volume while finding a marker that is robust to changes in a single variable, or in a subset of variables that are correlated with each other. For example, Hct is strongly correlated to Hgb and RBC and if all three were chosen in the set of variables, too much weight would be given to an increase in red cell mass as compared to plasma volume.

Figure 4:
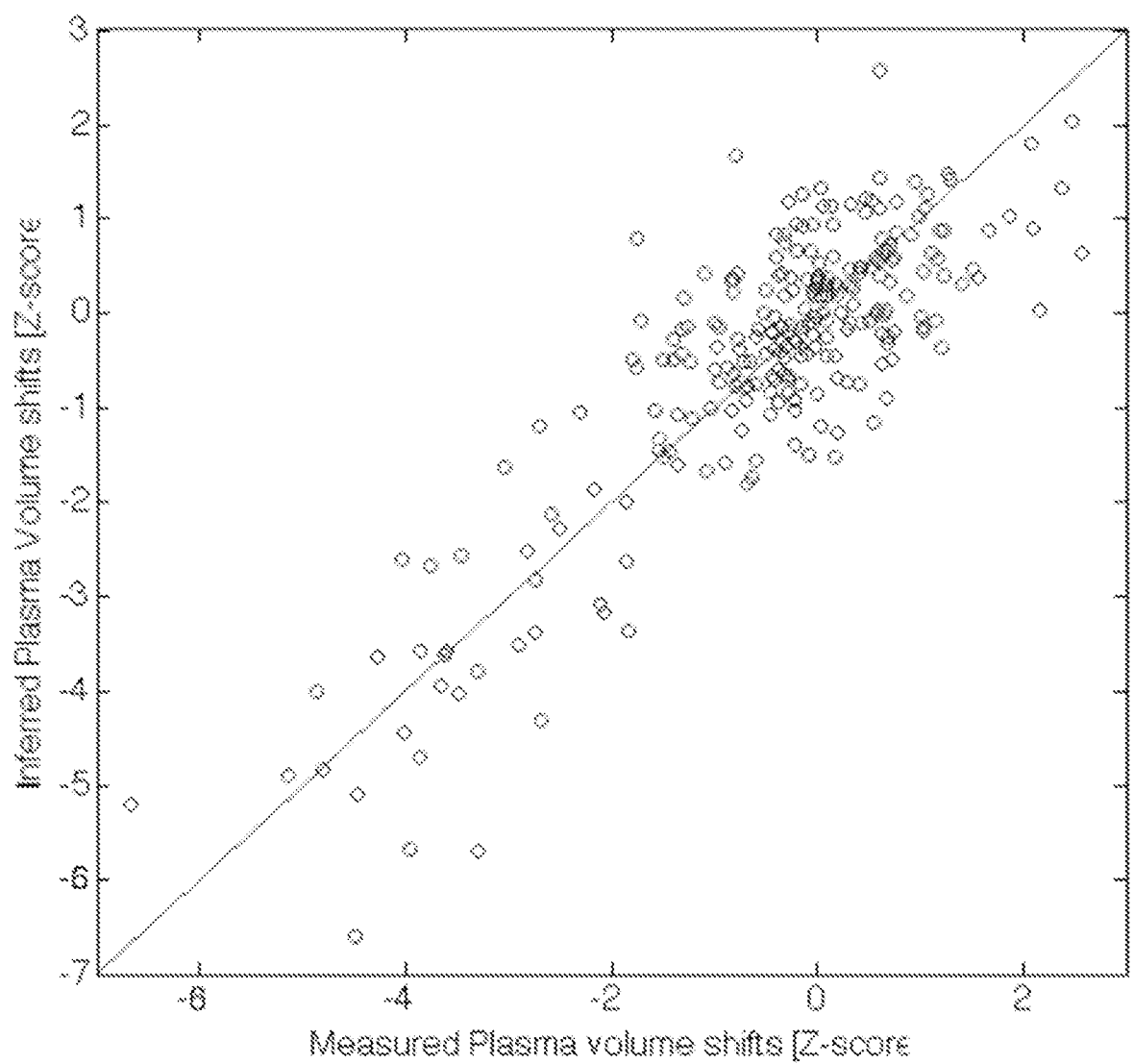
FIG. 4 represents the measured changes in plasma volume versus the changes in the marker of plasma volume (R2=0.75).

Two sets of biomarkers were found based on these criteria: a set of 8 biomarkers that includes HbC, Transferrin, Creatinine, Calcium, Platelets, LDL, Albumin and Total Protein, and a set of 15 biomarkers that includes, in addition to the 8 above, Cholesterol, Triglycerides, T4, WBC, PCT, NEUT, MONO. The first component of variance was able to explain 68%, respectively 69%, of the variations in plasma volume for the first, respectively second, set of biomarkers. In both cases, the marker with the highest contribution in the first component of variance was Total Protein. FIG. 4 shows the relation between the measured changes in plasma volume (x-axis) and the relative changes in the marker of plasma volume (y-axis). The values found after the acute exercise challenge can be seen at the bottom left, with a diminution in plasma volume up to 5-7 standard deviation of normal day-to-day variations in plasma volume.

The proposed multiparametric approach presents the great advantage to gain in specificity with the number of biomarkers included: the higher the number of independent biomarkers correlated to plasma volume, the better the specificity to plasma volume. In that context, the confidence in the model can be assessed: for example, if 7 out of 8 biomarkers present an increase in a Z-score, but the last a strong decrease, e.g. low platelets caused by an immune system problem, this inconsistency can be taken into account and a low weight attributed to the contribution of the platelet count in the computation of the marker of plasma volume. A weighting function has been determined as a normal probability density function applied on the residual of the PCA. The level of confidence becomes the exponential of the sum of this weighting function normalized between 0 and 1.

Discussion

The marker in plasma volume developed from the within-subject variations in a set of concentration-based variables measured in serum explains more than two thirds of the variations in plasma volume. Interestingly the derivation of the marker of plasma volume together with a classic measurement of hemoglobin concentration allows the estimation of the variations in hemoglobin mass. In other words, markers of both red cell volume and plasma volume can be readily be derived from a simple blood test to monitor both fluid balance and erythropoiesis. The method can be applied to all fields in which a strict balance between red cell and plasma volumes is required, including for hemodialysis treatment in patients with CKD, fluid therapy in patients undergoing major surgery and treatment and management of anemia.

Example 3

A male patient was tested at 8 occasions in a period of 7 months. Test number 7 was performed some minutes after an intense exercise session that was programmed to induce a large decrease in plasma volume. The 8 markers Transferrin, Albumin, Calcium, Creatinine, Total Protein, Platelets, Low Density Lipoprotein and Hemoglobin were measured in a serum sample collected for each test.

Figure 5:
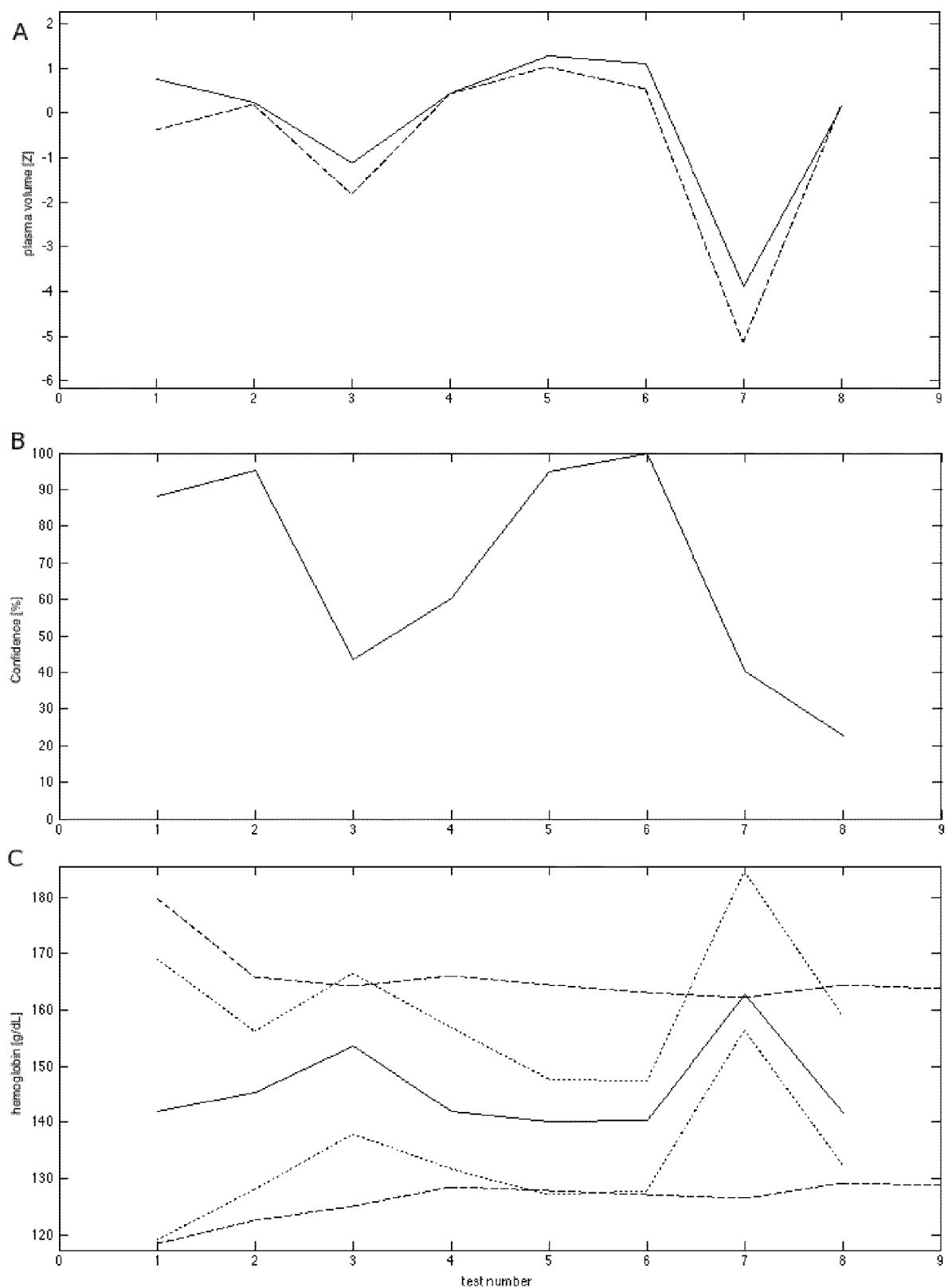
FIG. 5 Insert A shows the Z-score associated to plasma volume estimated from the individual variations in the 8 biomarkers. The Z-scores in plasma volume shifts estimated using the method presented herein (solid line) were then compared to the Z-scores calculated from the measurement of plasma volume shifts (dashed line). Insert B shows the confidence level associated to each estimated in plasma volume shifts. Insert C shows the values of hemoglobin (solid line). The dashed lines show the upper and lower limits of the personal reference intervals as obtained by the method but without correction for plasma volume. The dotted lines show the upper and lower limits of the personal reference intervals as obtained by the method with correction for plasma volume.

Insert A of FIG. 5 shows the Z-score associated to plasma volume estimated from the individual variations in the 8 biomarkers. The Z-scores in plasma volume shifts estimated using the method presented herein (solid line) were then compared to the Z-scores calculated from the measurement of plasma volume shifts (dashed line).

The CO-rebreathing method was used to measure the hemoglobin mass and in turn provide a reference of true plasma volume shifts to which the method is compared.

Insert B of FIG. 5 shows the confidence level associated to each estimated in plasma volume shifts.

Insert C of FIG. 5 shows the values of hemoglobin (solid line). The dashed lines show the upper and lower limits of the personal reference intervals as obtained by the method but without correction for plasma volume. The dotted lines show the upper and lower limits of the personal reference intervals as obtained by the method with correction for plasma volume.

The invention claimed is:

1. A method of determining plasma volume variation in a subject comprising the steps of:
   i) measuring values of one or more markers M in a full blood sample and/or in a serum sample obtained from said subject, wherein said one or more markers are selected from the group comprising: concentrations of hemoglobin (HbC), transferrin, creatinine, platelets, low-density lipoprotein (LDL), albumin, total protein, calcium, cholesterol, triglycerides, thyroxine, white blood cells, plateletcrit (PCT), neutrophils and monocytes;
   ii) determining heterogeneous factors of said subject or a group of subjects comprising: age, gender, ethnicity, body mass and genetic—and genomic information, wherein said factors are known to affect said one or more markers M in said subject or group of subjects;
   iii) applying Bayesian inference techniques using the values measured for the one or more markers of step i) to derive individual Z-scores for each marker M;
   iv) deriving from said individual Z-scores for each marker M a combined Z-score associated with plasma volume;
   v) comparing said Z-score associated with plasma volume to one or more reference ranges, wherein a deviation of said Z-score from the one or more reference ranges is indicative of plasma volume variation to normalize a serum- or plasma-based analytical test that is returned as a concentration.

2. The method of claim 1, wherein the one or more markers M are phenotypic biomarkers.

3. The method of claim 1, wherein the individual Z-scores for each marker represent individual variations around individual means.

4. The method of claim 1, wherein step i) measuring values of one or more markers M is performed multiple times at different times.

5. The method of claim 1, wherein derivations of individual reference Z-scores of step iii) for each marker M, are determined by $$Z(Mi) = \frac{M(i) - ME(i, j)}{\sqrt{VAR(i, j)}}$$

where each marker M is represented by Mi, and where ME(i,j) is the individual mean for subject j, VAR (i,j) the individual variance for subject j and Mi represents the value of one of the marker at time i.

6. The method of claim 1, wherein steps iii) and iv) are applied as follows
   establishing a first estimate of the individual Z-score (Z(Mi) estimate) associated with plasma volume calculated as the sum of the products of each individual Z-scores of all markers multiplied by the coefficients of the respective markers, determining residuals (R) in variations associated with each observation Mi as R(Mi)=Z-scores of all biomarkers-Σ(Z(Mi)estimate)×(respective marker's coefficients), establishing a weighting function associated with a consistency between the variations in each marker M calculated as a normality probability distribution of residuals in the variation of the markers, and calculating a Z score associated with plasma volume by weighting the first estimate of the Z-score (Z(Mi) estimate) with the weighting function.

7. The method of claim 6, wherein the coefficients of the respective marker are about 0.30 for HbC, about 0.23 for transferrin, about 0.23 for creatinine, about 0.25 for platelets, about 0.13 for LDL, about 0.25 for albumin, about 0.31 for total protein, about 0.20 for calcium, about 0.12 for cholesterol, about 0.064 for triglycerides, about 0.082 for thyroxine, about 0.48 for white blood cells, about 0.28 for PCT, about 0.19 for neutrophils and about 0.39 for the monocytes.

8. The method of claim 1, wherein said one or more markers are selected from the group comprising concentrations of HbC, transferrin, creatinine, platelets, LDL, albumin, total protein, and calcium, and wherein the respective marker's coefficients are 0.43 for HbC, 0.32 for transferrin, 0.33 for creatinine, 0.33 for platelets, 0.20 for LDL, 0.38 for albumin, 0.47 for total protein, and 0.31 for calcium.

9. The method of claim 1, wherein
- a Z-score higher than zero is indicative of hemodilution,
- a Z-score higher than 2.3 is indicative of strong hemodilution,
- a Z-score lower than zero is indicative of hemoconcentration, and
- a Z-score lower than −2.3 is indicative of strong hemoconcentration.

10. The method of claim 1, wherein the reference ranges are selected from the group comprising reference curves, reference data, z-scores and measurements for healthy or previously treated patients.

11. The method of claim 1 further comprising a step vi) of determining hemoglobin mass, red cell volume and/or blood volume, or monitoring fluid balance and erythropoiesis.

12. The method of claim 11, wherein the hemoglobin mass (HbM) is determined by a CO-rebreathing method.

13. The method of claim 11, wherein the red cell and blood volumes are determined by a joint measurement in the full blood sample of HbM, HbC and mean corpuscular hemoglobin concentration (MCHC) using the following formulas:

Red cell volume (L)=HbM(g)÷(MCHC(g/dL)*10);

Blood volume (L)=HbM(g)÷(HbC(g/dL)*10÷0.91).

* * * * *